(12) United States Patent
Cheryan et al.

(10) Patent No.: US 8,236,929 B2
(45) Date of Patent: Aug. 7, 2012

(54) METHOD AND SYSTEM FOR PRODUCTION OF ZEIN AND/OR XANTHOPHYLLS USING CHROMATOGRAPHY

(75) Inventors: Munir Cheryan, Urbana, IL (US); Aniket V. Kale, Champaign, IL (US); Fangyi Zhu, Urbana, IL (US); Philip L. Shane, Hudson, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 606 days.

(21) Appl. No.: 11/990,471

(22) PCT Filed: May 8, 2007

(86) PCT No.: PCT/US2007/011235
§ 371 (c)(1),
(2), (4) Date: May 5, 2009

(87) PCT Pub. No.: WO2007/133596
PCT Pub. Date: Nov. 22, 2007

(65) Prior Publication Data
US 2009/0215990 A1    Aug. 27, 2009

Related U.S. Application Data

(60) Provisional application No. 60/798,534, filed on May 8, 2006, provisional application No. 60/921,595, filed on Apr. 3, 2007.

(51) Int. Cl.
*C07K 14/00* (2006.01)
*C07C 35/21* (2006.01)

(52) U.S. Cl. .................... 530/373; 568/816; 514/2

(58) Field of Classification Search .................. None
See application file for complete search history.

(56) References Cited

U.S. PATENT DOCUMENTS

| | | |
|---|---|---|
| 3,069,443 A | 12/1962 | Witte |
| 3,523,138 A | 8/1970 | Grant |
| 3,962,335 A | 6/1976 | Kumar |
| 3,963,575 A | 6/1976 | Bulich |
| 4,093,540 A | 6/1978 | Sen Gupta |
| 4,224,219 A | 9/1980 | Van Blanton et al. |
| 4,414,157 A | 11/1983 | Iwama et al. |
| 4,486,353 A | 12/1984 | Matsuzaki et al. |
| 4,545,940 A | 10/1985 | Mutoh et al. |
| 4,624,805 A | 11/1986 | Lawhon |
| 4,716,218 A | 12/1987 | Chen et al. |
| 4,787,981 A | 11/1988 | Tanahashi et al. |
| 4,851,339 A | 7/1989 | Hills |
| 5,077,441 A | 12/1991 | Kuk et al. |
| 5,166,376 A | 11/1992 | Suzuki et al. |
| 5,254,673 A | 10/1993 | Cook et al. |
| 5,310,487 A | 5/1994 | LaMonica |
| 5,342,923 A | 8/1994 | Takahashi |
| 5,367,055 A | 11/1994 | Takahashi |
| 5,382,714 A | 1/1995 | Khachik |
| 5,410,021 A | 4/1995 | Kampen et al. |
| 5,482,633 A | 1/1996 | Muralidhara et al. |
| 5,510,463 A | 4/1996 | Takahashi |
| 5,545,329 A | 8/1996 | LaMonica |
| 5,580,959 A | 12/1996 | Cook et al. |
| 5,602,286 A | 2/1997 | Muralidhara |
| 5,648,564 A | 7/1997 | Ausich et al. |
| 5,747,544 A | 5/1998 | Garnett et al. |
| 5,773,076 A | 6/1998 | Liaw et al. |
| 5,847,238 A | 12/1998 | Muralidhara et al. |
| 5,876,782 A | 3/1999 | Sas et al. |
| 5,968,585 A | 10/1999 | Liaw et al. |
| 5,998,678 A | 12/1999 | Virgili |
| 6,169,217 B1 | 1/2001 | Cheryan |
| 6,191,293 B1 | 2/2001 | Levy |
| 6,262,284 B1 | 7/2001 | Khachik |
| 6,365,732 B1 | 4/2002 | Van Thorre |
| 6,433,146 B1 | 8/2002 | Cheryan |
| 6,495,140 B1 | 12/2002 | Collins et al. |
| 6,602,985 B1 | 8/2003 | McInnis |
| 6,610,831 B1 | 8/2003 | McInnis |
| 6,846,909 B2 | 1/2005 | Mairal |
| 6,911,564 B2 | 6/2005 | Khachik |
| 7,045,607 B2 | 5/2006 | Cheryan |
| 7,148,366 B2 | 12/2006 | Cheryan |
| 7,481,890 B2 | 1/2009 | Cheryan |
| 2002/0183490 A1 | 12/2002 | Cheryan |
| 2003/0176669 A1 | 9/2003 | Van Thorre |
| 2006/0173169 A1 | 8/2006 | Cheryan |
| 2007/0037993 A1 | 2/2007 | Cheryan |

FOREIGN PATENT DOCUMENTS

WO    WO 98/23567    6/1998

OTHER PUBLICATIONS

Amersham Biosciences Data file, "Sephadex® LH-20, High performance chromatography of steroids, terpenoids and low molecular weight peptides," pp. 1-8.
Amersham Biosciences Data file, "Sephadex® LH-60, Chromatography in organic solvents", pp. 1-6.
Cao et al., "Enzymatic Hydrolysis of Corn Starch After Extraction of Corn Oil with Ethanol," Applied Biochem and Biotech, pp. 39-47, 57/58 (1996).
Cheryan, M., abstract No. 9701992, 1997, "Abstract of Funded Research Fiscal Year 1997," [on-line], [retrieved on Sep. 22, 2000]. Retrieved from the internet: <URL: www.reeusda.gov/nri/pubs/archive/abstracts/abstract97/contents.htm and www.reeu.
Chien et al., "Oil Extraction of Dried Ground Corn with Ethanol," Chemical Engineering Journal, vol. 43 pp. B103-B113, 1990.
Chien et al., "Simultaneous Dehydration of 95% Ethanol and Extraction of Crude Oil from Dried Ground Corn," Cereal Chem. vol. 65 No. 6, pp. 484-486, 1998.
Concin et al., "Chromatographic behavior of aromatic compounds on Sephadex LH gels. Calibration of gel columns for determination of molecular weight distributions," J. Chromatography, 198, 1980, pp. 131-141.

(Continued)

*Primary Examiner* — Anand Desai
(74) *Attorney, Agent, or Firm* — Greer Burns & Crain Ltd.

(57) ABSTRACT

Methods and systems for obtaining zein and/or xanthophylls in highly pure form. Zein is first extracted from corn using aqueous ethanol. Suspended corn solids are separated, and the resulting extract is purified in a single size-exclusion chromatography step to separate impurities and produce substantially purified zein. The chromatography step may simultaneously produce substantially purified xanthophylls.

28 Claims, 7 Drawing Sheets

OTHER PUBLICATIONS

Craine et al., "Preparation of purified zein by adsorption-desorption," Cereal Chemistry 38, 1961, pp. 399-407.

Danzer et al., Purification of Zein on a Laboratory Scale by Charcoal or Gel Filtration, Cereal Chemistry, Mar. 1971, vol. 48 p. 118-120.

Dickey et al., "Hydrocyclone Separation of Dry-Milled Corn," Cereal Chem. vol. 74 No. 5, pp. 676-680, 1997.

Ganchev et al., "Characterization of A, B, $C_\alpha$ and $C_\beta$ Fractions, Isolated by Gel Chromatography of Zein", Comptes rendus del l'Académie bulgare des Sciences, Tome 25, No. 5, 1972, pp. 633-636.

Hojilla-Evangelista et al., "Sequential Extraction Processing of Flaked Whole Corn: Alternative Corn Fractionation Technology with Ethanol Production," Cereal Chem. vol. 69 No. 6, pp. 643-647, 1992.

Janshekar et al., "Fungal degradation of pine and straw alkali lignins," European J. Microbiol. Biotechnol., 14, 1982, 174-181.

Kwiatkowski et al., "Recovery of Corn Oil from Ethanol Extracts of Ground Corn Using Membrane Technology", JAOCS, vol. 82, No. 3 (2005), pp. 221-226.

Landry et al., "Sur les conditions d'obtention d'une zéine purifiée par charmatographie sur gels de dextranes alkyl", C.R. Acad. Sc., Paris t. 265 (Jul. 17, 1967 Série D), pp. 264-267.

Landry et al., "Zein of maize grain: I. Isolation by gel filtration and characterization of monomeric and dimeric species," Biochimie, 66, 1984, pp. 451-460.

Moros et al., "Analysis of xanthophylls in corn by HPLC," J. Agric. Food Chem., 50, 2002, pp. 5787-5790.

Mosse et al., "Recent research on major maize proteins: zeins and glutelins," In Cereal for Food and Beverages, G.E. Inglett, Ed., Academic Press, NY, 1980, pp. 255-273.

Seddon et al., "Dietary Carotenoids, Vitamins A, C and E and Advanced Age-related Macular Degeneration," JAMA vol. 272, No. 18 pp. 1413-1420, Nov. 9, 1994.

Sessa et al., "Improved methods for decolorizing zein," Industrial Crops and Products, 18, 2003, pp. 55-65.

Shukla et al., "Solvent extraction of zein from dry-milled corn," Cereal Chemistry, 77, 2000, pp. 724-730.

U.S. Appl. No. 11/801,223, filed May 2007, Cheryan et al.

Shukla et al., "Zein: The industrial protein from corn," Industrial Crops and Products, 13:171-192.

Singh et al., "Effect of Soak Time, Soak Temperature and Lactic Acid on Germ Recovery Parameters," Cereal Chem., vol. 73 No. 6, pp. 716-720.

Singh et al., "Extraction of Oil from Corn Distillers Dried Grains with Solubles," Transactions of the ASAE, vol. 41, No. 6 (1998), pp. 1-3.

Singh et al., "Membrane Technology in Corn Refining and Bioproduct-processing," Starch/Starke, vol. 50, No. 1, pp. 16-23, 1998.

Singh et al., "Membrane Technology in Corn Wet Milling," Cereal Foods World, vol. 42, No. 7, pp. 520-525 (1997).

Kale, Aniket V., et al., "Rapid Analysis of Xanthophylls in Ethanol Extracts of Corn by HPLC," Journal of Liquid Chromatography & Related Technologies, 30; 1093-1104, 2007.

Moros, Eleftherios E., "Analysis and Extraction of Xanthophylls from Corn," Master's Thesis, pp. 1-2 and 63-90, University of Illinois, Urbana, Illinois, 2000.

Moros, E. E., et al., "Analysis of Xanthophylls in Corn by HPLC," Journal of Agriculture and Food Chemistry, 2002, 50, 5787-5790.

Tsui, Eliza M., et al., "Membrane processing of xanthophylls in ethanol extracts of corn," Journal; of Food Engineering, 83 (2007), 590-595.

METHOD AND SYSTEM FOR PRODUCTION OF ZEIN AND/OR XANTHOPHYLLS USING CHROMATOGRAPHY

PRIORITY CLAIM

This application claims the benefit of U.S. Provisional Application Ser. No. 60/798,534, filed May 8, 2006, and U.S. Provisional Application Ser. No. 60/921,595, filed Apr. 3, 2007, under 35 U.S.C. §119.

STATEMENT OF GOVERNMENT INTEREST

This invention was made with Government assistance under U.S. Department of Agriculture (USDA) Grant No. AG 2004-35503-14116. The Government has certain rights in this invention.

BACKGROUND ART

The present invention generally concerns production of proteins and/or xanthophylls from corn.

Corn is one of the major crops in the United States. About 25% of corn is converted to food, feed, and industrial products. Ethanol production from corn by the dry-grind process has increased exponentially recently and is expected to reach 7.5 billion gallons by 2012. At present, a dry-grind ethanol plant typically produces three products: ethanol, carbon dioxide, and distillers dried grains with solubles (DDGS). Since operating costs presently are almost equal to the revenue from ethanol, any profit is derived from the coproducts, as well as from subsidies and tax waivers. The dry-grind ethanol process currently is a low-profit operation, and there is a need for new technologies and additional coproducts to improve its profitability.

Protein forms about 10% of the dry weight of corn. It is composed of zein (a highly hydrophobic protein, soluble in isopropanol or ethanol) and glutelin (soluble in aqueous alkaline solutions), with lesser amounts of globulins and albumins. Zein is unique in that it is insoluble in water except in the presence of alcohols or high concentrations of alkali or anionic detergent. It is a protein with several existing and potential applications in the food, pharmaceutical, and biotechnology industries. As nonlimiting examples, zein has great potential in biodegradable films and packaging materials, chewing gum, pharmaceutical gel tablets, and a variety of other markets, as identified by R. Shukla and M. Cheryan, "Zein: The industrial protein from corn," Industrial Crops and Products, 13: 171-192.

However, it is desirable to substantially improve the purity of the obtained zein to command a higher price and volume. Further, it is desirable to reduce the cost of production.

Various methods of producing zein from corn have been discussed in articles such as those by R. Shukla and M. Cheryan, above, and in several patents. Most of these methods use aqueous solutions of ethanol to do a first extraction of the zein from ground, flaked, or otherwise size-reduced whole corn or corn processing by-products such as corn gluten meal. However, the ethanol solvent co-extracts several other compounds such as xanthophylls, polyamines, lipids, and other compounds that have not yet been identified. Thus, the various processes are distinguished mainly by the subsequent methods of separation and purification to increase purity of zein from about 10-50% to about 90%.

For example, U.S. Pat. No. 6,433,146 to Cheryan, incorporated herein by reference, describes a method for extracting zein from corn using aqueous ethanol, followed by a separation (e.g., filtration or centrifugation) to remove suspended particles, and typically followed by one or more membrane separation steps using ultrafiltration and/or nanofiltration membranes to purify the zein by removal of low-molecular weight impurities. In preferred methods, the ethanol is recycled. U.S. Pat. No. 6,846,909 to Mairal also describes a process for purifying zein using membranes.

U.S. Pat. Nos. 6,602,985 and 6,610,831 describe a process that uses water to remove water-soluble components from ground corn or corn gluten meal, followed by ethanol extraction of zein and treatment of crude zein with activated carbon. However, zein yield in such a process can be as low as 25%, since zein may be bound to the carbon.

U.S. Pat. No. 5,580,959 to Cook et al. describes a process of purifying zein using enzymatic starch hydrolysis, alkaline treatment, ethanol extraction, and activated carbon adsorption. U.S. Pat. Nos. 5,342,923, 5,367,055, and 5,510,463 to Takahashi disclose using acetone, hexane, and other organic or hydrocarbon solvents to remove oil, color pigments and odor compounds from corn gluten meal followed by extraction of zein using aqueous ethanol. In these patents, the protein is exposed to enzyme or high pH or organic solvents or strong adsorbents, which may change the natural conformation and/or composition of the protein. This, in turn, may limit the potential uses of the extracted zein.

U.S. Pat. No. 4,624,805 to Lawhon teaches extraction and purification of corn endosperm proteins using ultrafiltration. However, the product is a mixture of zein and glutelin.

Generally, conventional purification methods usually do not provide high yields and purity simultaneously, nor do they produce a zein that is devoid of xanthophylls.

One of the coproducts in preferred embodiments of the present invention is xanthophylls such as lutein, zeaxanthin, and beta-cryptoxanthin. Lutein and zeaxanthin have numerous potential health benefits, including mitigating age-related macular degeneration, cardiovascular damage, and certain forms of cancer. Xanthophylls cannot be synthesized by the human body and must be obtained from foods such as fruits, vegetables, and eggs, or from dietary supplements containing chemical- or fermentation-derived compounds. Among natural sources, egg yolk and corn contain the highest molar levels of lutein and zeaxanthin (more than 85% of the total carotenoids). Most sources of xanthophylls other than corn are rich in either lutein or zeaxanthin, but not both.

The major commercial source of xanthophyll today is marigolds. U.S. Pat. No. 6,262,284 to Khachik describes extraction of lutein using an alkaline organic solvent of tetrahydrofuran containing ethanol and KOH maintained at pH 12. U.S. Pat. No. 6,911,564 to Khachik describes methods of chemical conversion of lutein to anyhydroluteins. In both patents, Khachik describes purifying lutein by column chromatography using n-silica gel and mobile phases such as $C_5$-$C_7$ hydrocarbons or petroleum ether in combination with acetone or methyl ethyl ketone or ethyl acetate or tetrahydrofuran or $C_4$-$C_6$-ethers. However, the xanthophylls in marigolds are in an ester form and require additional steps to obtain the pure form. The product is also quite unstable and cannot be processed into very high concentrations of the xanthophylls. Further, marigolds produce mainly lutein and not zeaxanthin, and the methods taught by these patents use a complicated series of steps and expensive solvents.

SUMMARY OF THE INVENTION

A method and system for obtaining zein and/or xanthophylls in highly pure form is provided. The zein and/or xanthophylls are first extracted from corn using aqueous ethanol.

Suspended corn solids are separated, and the resulting extract is purified in a single size-exclusion chromatography step to separate impurities and produce substantially purified zein, including pure (white) zein. The chromatography step may simultaneously produce substantially purified xanthophylls.

BRIEF DESCRIPTION OF THE DRAWINGS

Other features, objects, and advantages of the invention will be apparent to those skilled in the art from the following detailed description and by reference to the drawings, of which.

BEST MODE OF CARRYING OUT THE INVENTION

It is possible to extract zein and xanthophylls with 70-85% aqueous ethanol with little or no co-extraction of corn oil. The zein and xanthophylls may then be purified using, for example, membrane technology. Several stages of ultrafiltration and nanofiltration membranes may be needed, as well as diafiltration, to obtain a desired (e.g., >90%) purity of zein. In addition, because most of the co-extracted impurities have similar molecular sizes as the xanthophylls, membranes alone cannot produce a highly pure xanthophylls stream.

In corn, xanthophylls are preferentially bound to zein, and as a result, extraction and purification of xanthophylls from corn also results in the simultaneous extraction and purification of zein, and vice versa. Thus, according to preferred embodiments of the present invention, zein can be extracted and substantially purified, while simultaneously providing highly pure xanthophylls.

According to embodiments of the present invention, chromatography is used to produce substantially pure zein and xanthophylls. Chromatography has the advantage of being able to achieve high resolution (i.e., a high degree of separation between zein, xanthophylls, and impurities) leading to high purity, while not requiring harsh processing conditions such as extremes of temperature, pressure, or shear that could otherwise lower product quality. In preferred embodiments of the present invention, production and purification of zein and xanthophylls can be achieved simultaneously by chromatography, and by using only raw materials available in a dry-grind ethanol plant, such as ethanol and whole ground corn.

Generally, chromatography separates components of a complex mixture by partitioning the target compounds between a flowing fluid (the mobile phase) and a solid stationary matrix, which can be an adsorbent, ion-exchange resin, porous solid, or a gel adsorbent. Individual solutes interact with the solid phase in different ways and rates, and they eventually come out of the column in separate bands.

Previously, zein has been separated using cation exchange chromatography, as disclosed in Craine et al., "Preparation of purified zein by adsorption-desorption," Cereal Chemistry 38, 1961, pp. 399-407. In this method, ground corn was defatted and then extracted with 70% ethanol. The corn extract was processed with an Amberlite IRC-50 column using a salt (NaCl) gradient. The purity of the product was 85%, and the yield was 86%. The remaining zein was irreversibly bound to the resin.

Landry et al, "Sur les conditions d'obtention d'une zein purifiee par chromatographie sur gels de dextranes alkyls," Compt. Rend. Acad. Sci., t.265 (17 Juillet), 1967, pp. 264-267, and Landry and Guyon, "Zein of maize grain: I. Isolation by gel filtration and characterization of monomeric and dimeric species," Biochimie, 66, 1984, pp. 451-460, proposed a protocol that used a complicated series of eight liquid extractions that included organic solvents such as ether and acetone, followed by two size exclusion chromatography steps with the Sephadex LH-20 resin utilizing a different mobile phase in each step. L. A. Danzer and E. D. Rees, Purification of zein on a laboratory scale by charcoal or gel filtration, Cereal Chemistry, 48, 1971, pp. 118-120, discloses a size exclusion resin followed by treatment with charcoal to separate zein from corn extracts, obtaining zein of 90% purity.

Sessa et al., Improved methods for decolorizing zein, Industrial Crops and Products, 18, 2003, pp. 55-65, discloses decolorizing zein in several ways, such as supercritical fluid extraction, ultrafiltration, activated carbon, and column chromatography with Sephadex LH-60. However, the raw material used was commercial zein (Freeman FC 4000), which is already substantially pure (typically 85-90% protein). Thus, it was not demonstrated that the Sephadex LH-60 would have purified zein from an ethanol extract of whole raw corn or corn by-products in which zein purity is typically smaller; e.g., only 35-50% (see R. Shukla, M. Cheryan, and R. E. DeVor, "Solvent extraction of zein from dry-milled corn," Cereal Chemistry, 77, 2000, pp. 724-730; R. Shukla and M. Cheryan, "Zein: The Industrial protein from Corn," Industrial Crops and Products, 13, 2001, pp. 171-192). In fact, the pore size and fractionation range of the Sephadex LH-60 is too large for effective purification of the zein from such extracts. According to the manufacturer's specifications and scientific literature, the molecular weight exclusion limit of the LH-60 is shown as 18,000-20,000.

In addition, Sessa et al. measured loss of color pigments by absorbance at a wavelength of 325 nm, and not at the 450 nm wavelength that is more representative of corn-derived xanthophylls. Thus, it was not definitively demonstrated that xanthophylls were removed.

J. Mosse and J. Landry, "Recent research on major maize proteins: zeins and glutelins," In Cereal for Food and Beverages, G. E. Inglett, Ed., Academic Press, NY, 1980, pp. 255-273, used Sephadex G-100 and Sephadex G-200 for separating zein monomers and dimers. These resins also have exclusion limits that are too large for efficient purification of whole zein.

Chromatographic separation can be done based on size, charge, affinity, or hydrophobicity difference of the desired products. Due to the large difference in the molecular weights of the compounds to be separated, viz., xanthophylls (~560) and zeins (>17 kDa), a preferred chromatographic method according to the present invention for zein and xanthophylls is size-exclusion chromatography (SEC), of an appropriate molecular weight exclusion limit. It will be understood that the term "size exclusion" refers generally to the concept of separation based on size. This may be performed, for example using resins, gels, and other media of various compositions. More particularly, SEC is based on differences in solute size and shape, and may be commonly referred to as gel permeation, though other media may be used.

The stationary phase (gel matrix) has pores of a defined diameter that excludes larger molecules which remain in the void volume of the gel. Molecules that are smaller than the pore will enter the pore and be retarded. During elution, the excluded molecules such as proteins will exit with the eluent in the first retention volume. Theoretically, there would be no interaction of the feed and the column material. Thus, there would be no conformational changes in the structure of the products, which could be an important attribute for various applications.

In preferred embodiments of the present invention, the preferred raw material is corn (Maize) because the xanthophylls in corn contain both lutein and zeaxanthin, which are more desirable for applications such as, but not limited to, treating age-related macular degeneration. In addition, preferred methods use a more benign solvent (aqueous ethanol) than that, say, of the '564 and '284 Patents to Khachik (above), and the same solvent preferably is used throughout the preferred process. U.S. Pat. No. 6,169,217, to Cheryan, which is incorporated by reference herein, describes a process for extracting xanthophylls with aqueous ethanol followed by membrane filtration for concentration and purification.

The present inventors have discovered that extensive liquid extractions of corn or corn-based raw material such as those taught by Landry et al. and Landry and Guyon, above, are not necessary, and that a single liquid extraction with one solvent is sufficient to maximize yield of zein. Further, the present inventors have found that the resulting ethanol extract, after suitable separation to remove suspended matter, can be used directly on a chromatography column under the appropriate operating conditions to obtain effective separation and purification with higher yields. In addition, preferred embodiments of the present invention utilize a single solvent for the elution, preferably the same solvent that was used in the extraction. This will maximize the life of the resin, unlike a process that uses different mobile phases, which may result in sequential swelling and shrinking of the resin.

In an exemplary method and system for obtaining zein and/or xanthophylls in highly pure form, zein and/or xanthophylls are first extracted from corn using aqueous ethanol. Suspended corn solids are separated, and the resulting extract is purified in a single size-exclusion chromatography step to separate impurities and produce substantially purified zein, including pure (white) zein. The chromatography step may simultaneously produce substantially purified xanthophylls.

Figure 1:
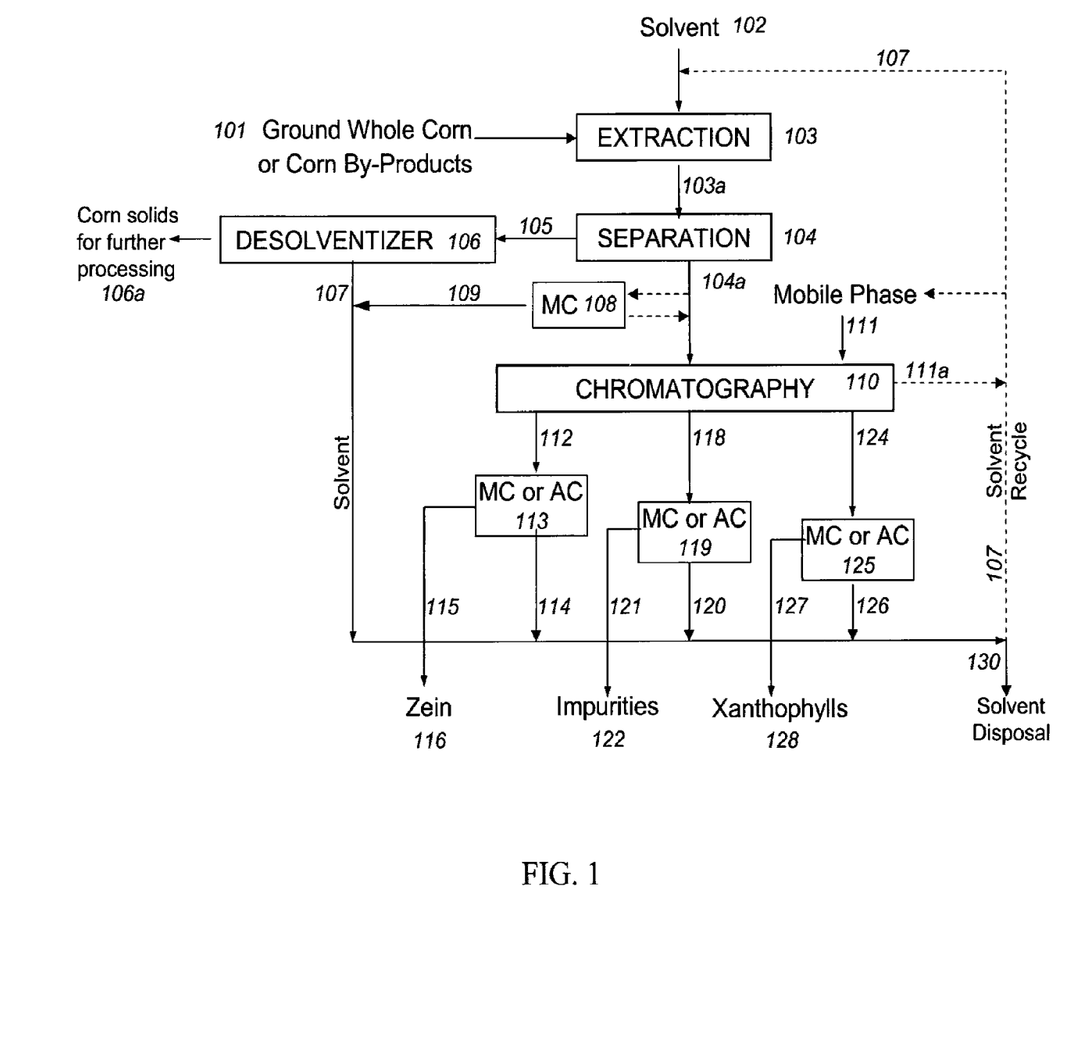
FIG. 1 is a general schematic showing steps for the production of pure zein and xanthophylls by chromatography, according to embodiments of the present invention.

Referring now to the drawings, a general schematic of a preferred embodiment of the invention is shown in FIG. 1. The feedstock is a corn product 101, which may be ground whole corn, or corn processing coproducts such as partially degermed corn, corn gluten meal (a product of the corn wet milling industry), or distillers dried grains (DDG) with or without solubles (DDGS) (a by-product of the dry-grind ethanol industry). The feedstock may be prepared for the extraction, for example, by grinding or flaking to the appropriate size and/or by other operations known to those skilled in the art. The prepared feedstock is extracted with a suitable solvent 102 in an extraction step 103 to specifically extract the prolamine zein and/or xanthophylls. The preferred solvent 102 is aqueous ethanol, which is a mixture of 40% to 95% (by volume) ethanol and water. The present inventors have found that 60-90% ethanol, and preferably 70% ethanol, is more suitable if zein is the desired product. If xanthophylls is the desired product, 85-92% ethanol may be more suitable as described in the '217 Patent. Isopropanol is another solvent that has been found to be effective in extracting zein. The main raw materials 101 and 102 are best obtained in-house from a dry-grind ethanol plant.

For the extraction step 103, the corn product 101 and the solvent 102 are mixed in an extractor, which may be a batch mixer for small production capacities and a continuous extractor for large capacities. If done in a batch extractor, the resulting corn solvent mixture (e.g., ethanol-corn slurry) 103a is sent through a first separation or clarification step 104. The clarification step 104 may be, for example, centrifugation, conventional filtration, or membrane microfiltration, such as described in U.S. Pat. No. 6,433,146, to Cheryan. The objective of the clarification step 104 is to remove the suspended solids in the extract, shown in FIG. 1 as a solids stream 105, leaving only dissolved corn components in a liquid stream 104a that is a clarified extract, referred to in the subsequent description as a "corn extract," of which the major component is the alcohol soluble proteins called zein. The non-zein components in the corn extract 104a may include fatty acids, sugars, amino acids, color pigments, carotenoids, lipid components and the like.

The solids stream 105 from the clarification step 104 is sent to a desolventizer 106 to remove the solvent adsorbed or bound to the solids. The solids stream 106a from the desolventizer unit 106 may be processed as necessary depending on the raw material. If ground corn is the raw material, for example, this stream 106a may be sent for production of dextrose and/or for production of bioproducts by fermentation such as ethanol. If the raw material is corn gluten meal in a wet milling plant, then the solids stream 106a would contain mostly the alkali soluble protein glutelin and corn fiber. This residue may be added to a corn gluten feed stream. On the other hand, if the raw material is DDGS, then the solids stream 106a would be a protein-fiber mixture containing protein, oil, minerals, and by-products of ethanol fermentation such as yeast and nutrients. It could be dried and sold as animal feed. Solvent 107 obtained from the desolventizing step 106 may be recycled in the system, or it may be sent for solvent disposal or to the distillation column in an ethanol plant.

The corn extract 104a from the clarification step 104 is a solution containing dissolved solids rich in zein. This corn extract 104a is now suitable to be processed directly by chromatography or, depending on the concentration of the zein and the properties of the chromatographic resin and equipment that is used, the corn extract may optionally be processed by membrane concentration (MC) step 108, to provide a concentrated extract. Membrane concentration may include ultrafiltration, nanofiltration, or reverse osmosis. The objective of the membrane concentration step 108, if used, is to obtain the desired concentration of zein that will maximize the productivity of the chromatographic system. For example, if ultrafiltration is used in the membrane concentration step 108, it will partially purify the zein by removing lower molecular weight components. If nanofiltration or reverse osmosis is used in the membrane concentration step 108, then the retentate will be essentially all the solids in the corn extract (liquid stream) 104a at a higher concentration. The permeate 109 from the membrane concentration step 108 is relatively pure solvent if nanofiltration or reverse osmosis is used, and this solvent can be recycled 107 in the plant. The membrane concentration step 108 may not be necessary if the amount of solvent 102 used in the extraction step 103 is reduced to a minimum while obtaining acceptable yields. This can be accomplished by using continuous extraction instead of batch extraction, for example, using continuous extractors manufactured by Crown Iron Works, or DeSmet, or Lurgi, and the result sent to the separation step 104.

Either directly after the separation step 104, or after the membrane concentration step 108, the corn extract 104a is processed by chromatography 110, which separates the components of the corn extract into two or more fractions. The preferred stationary (solid) phase for the chromatography 110 is a size-exclusion resin with a preferred molecular weight exclusion limit of less than 5000. One example is the LH-20 resin manufactured by GE Healthcare, which has a molecular weight exclusion limit of 4000-5000 (Amersham Biosciences data file on LH-20; Coocni et al. 1980; Jansshekar et al. 1982). Another example is the HW40 resin manufactured by Tosoh Biosciences. The important criterion is that the resin must be stable in aqueous ethanol, since aqueous ethanol will be the mobile phase used to elute components from the column. Suitable design of columns for the chromatography step 110 will be apparent to those of ordinary skill in the art.

The mobile phase 111 preferably is the same or similar composition to the solvent used for extraction; i.e., it is preferably about aqueous ethanol at about 70% concentration (by volume). This is believed to be a major advantage of preferred embodiments of the invention, since it avoids having to handle more than one solvent in the manufacturing plant.

Another unique characteristic of preferred embodiments is that with the appropriate process conditions in the chromatographic system, two valuable products, zein and xanthophylls, can be produced simultaneously. As will be seen in the examples provided herein, in addition to the extraction solvent, three distinct and well-separated fractions with baseline separations may be obtained: zein, xanthophylls, and a third fraction that contains substantially all components in the extract other than zein and xanthophylls, which is labeled herein as the "impurities" fraction. Particularly, the first fraction to elute from the column is the extraction solvent in the void volume of this column, which can be recycled at step 111a. The second fraction to be eluted is the substantially purified zein 112, because it is excluded from the pores of the selected resin. The third fraction is the impurities 118. The fourth fraction is the substantially purified xanthophylls 124. By this step, a preferred process has substantially enhanced the value of the coproducts from a typical corn processing plant, especially a dry-grind ethanol plant.

The three fractions 112, 118 and 124 are very dilute due to the volume of mobile phase (e.g., aqueous ethanol) used for elution. Thus, these fractions may be concentrated as shown in concentration steps 113, 119, and 125 prior to further processing. We have found that membrane concentration (MC) and/or adsorption chromatography (AC) can be used for this purpose. Membrane concentration includes ultrafiltration, nanofiltration, or reverse osmosis membranes. Membranes such as the DK from GE, or selected SR and HFM membranes from Koch Membrane Systems or PCI membranes provided by ITT Sanitaire have been found to be suitable. Conditions for membrane concentration will depend on which type of membrane system is used. Such conditions will be appreciated by those of ordinary skill in the art. The permeate streams 114, 120, and 126 from the concentration step 113, 119, 125 may be recycled back into the system as solvent 107. If adsorption chromatography (AC) is used as the concentration step 113, 119, 125, suitable resins may be selected from the Rohm and Haas XAD series or the Mitsubishi HP and SP series. Particular conditions will depend on the type of adsorbent system used, and such conditions will be appreciated by those of ordinary skill in the art. Ethanol may be recycled 107 from the AC step as well.

The retentate streams 115 and 121 from the concentration steps 113, 119 may be dried by using a suitable drier designed to handle solvents. The final dry zein product 116 is a highly pure, white, natural, whole zein. Concentrated impurities 122 from the concentration step 119 may be recycled to corn solids stream 106a or dried for sale. The concentrated xanthophylls stream 127 may be sold as a concentrated liquid or dissolved in a suitable medium such as vegetable oils or in encapsulated form. The solvents recovered from the drying steps may be recycled as solvent 107 or disposed 130 as appropriate.

Various embodiments and methods of practicing this invention are provided in the following examples. It is to be recognized that these examples are for illustrative purposes and the invention is not to be limited to those methods described. Those skilled in the art can adopt several variations of the described operating conditions and apparatus to achieve substantially the same or comparable results.

EXAMPLE 1

In an experiment evaluating an exemplary method for extraction of zein and xanthophylls from corn, an extraction method was adapted from R. Shukla, M. Cheryan, and R. E. DeVor, "Solvent extraction of zein from dry-milled corn," Cereal Chemistry, 77, 2000, pp. 724-730. Raw whole corn (yellow dent #2) was obtained from Anderson Grain Co., Champaign, Ill. The corn was ground using a bench top hammer mill, IKA MF 10.2 (IKA Works Inc., Wilmington, N.C.) with a 1 mm mesh. Ethanol (200 proof; USP grade) was procured from Aaper Alcohol and Chemical Co., Shelbyville, Ky. The water was distilled, deionized, and microfiltered using a 0.2 µm Maxi Capsule Filter (Pall Gelman Lab, Ann Arbor, Mich.). Extraction was done in an Erlenmeyer flask using a solvent:solids ratio of 4:1 (4 L of 70% ethanol per kg of corn) at 40° C. for 30 min. A Nuova II stirring hot plate (Thermolyne, Dubuque, Iowa) was used for temperature control and mixing. The slurry was then filtered with Whatman paper #1 (11 µm average pore diameter, Whatman Inc., Clifton, N.J.). The extract was then stored at 40° C. in an Oakton stable temperature oven (Oakton, USA) until use to avoid any precipitation. The extract was microfiltered with a 0.45 µm hydrophilic low protein binding PTFE filter (LCR, Millipore Corp., Bedford, Mass.).

For chromatography, a semi-prep Waters (Waters Corporation, Milford, Mass., USA) system including a Waters 600E multisolvent delivery system (600E pump with flow range 0-20 mL/min and a 600E pump controller) and a Waters 2996 PDA detector (equipped with a light source of Deuterium lamp with a flow cell capacity of 10 µL) was used. The system was connected to a personal computer with Waters Empower software for the data analysis. Manual injections were carried out directly through the inlet manifold valve. The injection volume was set to 50 mL by controlling the sample injection time at a constant flow rate of 6.25 mL/min to 8 min.

An Omnifit column (2.5 cm diameter, 100 cm length, 491 mL column volume) was purchased from Western Analytical Inc. (Murrieta, Calif.). It was packed with LH-20 resin according to the manufacturer's instructions. The cross-linked hydroxypropylated dextran based Sephadex LH 20 (GE Healthcare-Biosciences, Piscataway, N.J.) was used, since it is stable in aqueous ethanol concentrations over 70% ethanol and has a molecular weight exclusion of less than 10 kDa. It was equilibrated with 70% aqueous ethanol solution at room temperature. Fifty milliliters of the corn extract was injected into the column. The mobile phase was pumped into the column using a Waters 600E pump at room temperature and a flow rate of 375 mL/h. Samples were collected every 3 min for 1.5 column volumes elution.

For comparison purposes, zein with a protein content of about 90% (F4000) was obtained from Freeman Industries, Tuckahoe, N.Y. Showa zein with a protein content of over 90% was obtained from Showa Sangyo Corp., Tokyo, Japan. Xanthophylls were obtained from DSM Nutritional Products, Basel, Switzerland. The eluents used in the experiment were filtered using a 0.2 µm filter (FGLP, Millipore Corp., Bedford, Mass.).

To analyze the results, the absorbance of the samples was measured with the PDA detector at three wavelengths: 280, 310, and 450 nm. The chromatograms obtained at 280 nm represent the impurities, 450 nm represents the xanthophylls. The samples were sufficiently dilute and did not require further dilution for analysis.

The total solids in the sample were analyzed using gravimetric method. The liquid samples were placed in a hood for 6 h to evaporate the ethanol in the sample. The samples were then dried at 103° C. for 6 h and weighed to determine the solids content of the original sample.

Crude protein was analyzed using a Leco FP-528 Nitrogen Combustion Analyzer (Leco, St. Joseph, Mich.) by the AAOC method (AOAC, 2000). Protein was calculated as nitrogen× 6.25 and was assumed to be zein.

Protein molecular weight distribution was obtained using an automated electrophoresis system (Agilent 2100 Bioanalyzer, Agilent Technologies, Palo Alto, Calif.). This system is based on the proteins moving through microfluidic channels of the gel on a chip at different velocities based on their size under an electric current. Theoretically, all proteins have the same shape and charge due to SDS or LDS micellization and have a fluorescent marker attached. The fluorescence detection gives the distance traveled by each protein based on its molecular size (assumed to be directly proportional to the weight). This system provides the gel representation of the results as well as the electropherograms. The sample preparation is done as described by the manufacturer. No mercaptoethanol was used in the exemplary sample preparation.

Routine determination of xanthophylls concentration was done by spectroscopy at 450 nm. Individual isomers were analyzed using HPLC. The HPLC column was a 4.6 mm×250 mm C-30 carotenoid column (Waters Inc., Wilmington, N.C.). A guard column (4 mm×23 mm) containing the same packing material as the C-30 column was installed ahead of the carotenoid column. The solvents were HPLC grade methanol and methyl-tert-butyl-ether (MTBE, Fisher Scientific, Pittsburgh, Pa.). A gradient system was used involving two mobile phases. Mobile phase A was pure methanol and mobile phase B pure MTBE. The initial values were 90% of A and 10% B, to 50% A and 50% B in 16 min, followed by a cleaning with 9% A and 91% B for 5 min. The flow rate was 1.0 mL/min, and the temperature was 25° C. during the entire run. All samples were injected via a 100-µL loop using a 1-mL syringe.

Figure 2:
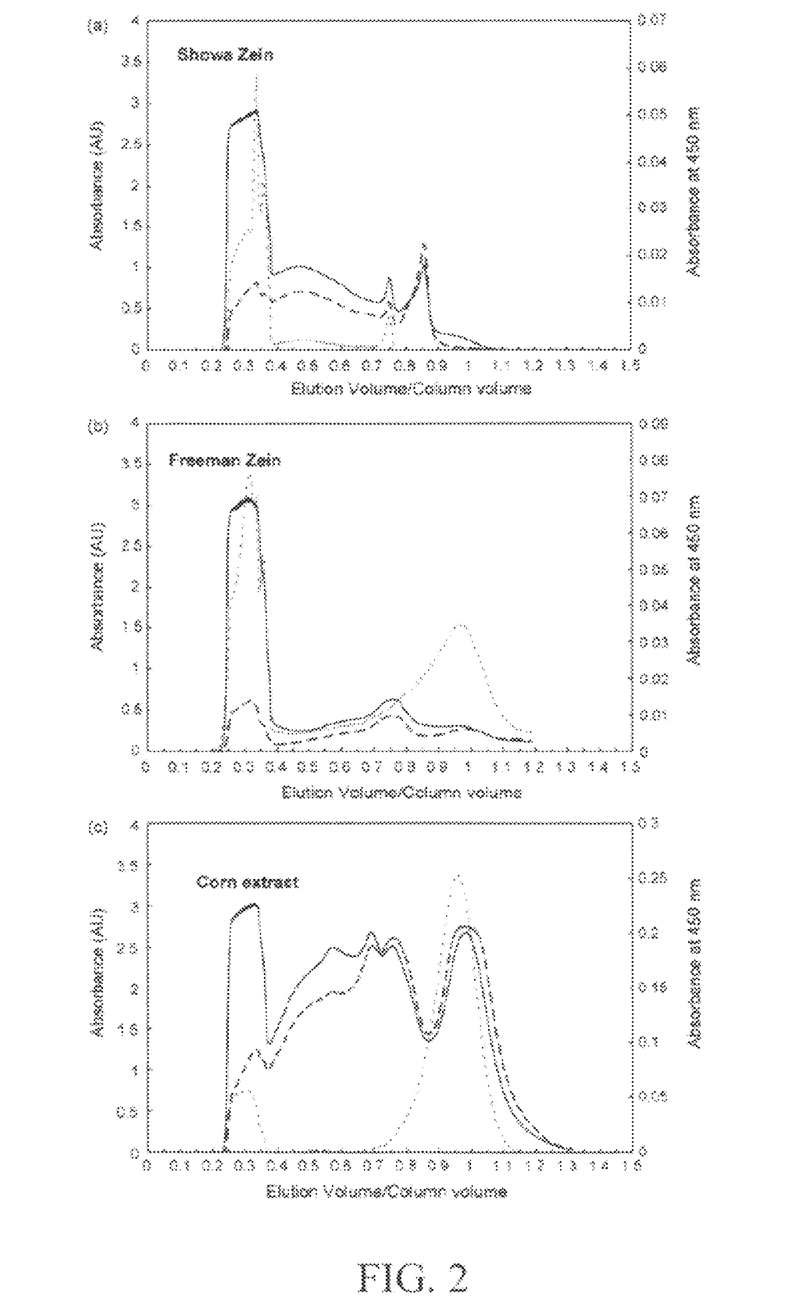
FIG. 2 is a set of chromatograms of a) Showa zein at a concentration of 1.5% (w/v), b) Freeman zein at a concentration of 1.5% (w/v) and c) corn extract containing zein at a concentration of 0.7% (w/v)

The separation capabilities of the chromatography system were evaluated using the LH-20 resin packed in an Omnifit column. Fifty milliliters of commercial zeins (Showa and Freeman Yellow~F4000) prepared in 70% ethanol to a concentration of 1.5% (w/v) and the corn extract (containing about 7 g/L of zein) were injected onto the column. The chromatograms obtained for each of the samples are shown in FIG. 2. Zein is represented by the chromatograms at 280 nm (black solid line). In all cases in this exemplary embodiment, it is completely excluded from the column and passed through it with minimal interaction with the hydrophilic media. In addition, due to its size, it could not pass through the pores of the LH-20 resin, which are ~1 nm in size. Zein is apparently the only compound in the extract that is larger than the molecular weight cut-off of the resin, and hence the purity of the zein is high.

On the other hand, the xanthophylls (represented by the dotted red line in FIG. 2) eluted after one column volume of elution. This may be because LH-20 has lipophilic ("L") propyl groups and hydrophilic ("H") hydroxyl groups. The LH-20 resin separates organic compounds of low molecular weight by adsorption using its inherent hydrophobicity. Thus, the xanthophylls were adsorbed by the resin and eluted slowly after one column volume. FIG. 2 also shows the relative amounts of xanthophylls in the three products. The Showa zein is manufactured with a series of solvent washings to remove the color and non-zein impurities. It has the lowest level of xanthophylls and is the whitest in color.

The fractions eluting after the zein (the "impurities" fraction) showed a high absorbance at 280 nm, especially with the corn extract and to a lesser extent with the commercial zeins. However, the nitrogen content was negligible in the impurities fractions, as will be discussed below. The peak spectra maximum is at 310 nm for this fraction. In FIG. 2, 310 nm is represented by a blue dashed line. The impurities could be polyamine putrescine compounds, which show a very high UV absorbance around 320 nm. However, these compounds amount to about 115 ppm in corn and are found mostly in the pericarp, with a small amount (~7%) in the endosperm. Thus, these compounds will be in the ppm or even ppb levels in our extract. The oil content in the extract is negligible, as observed previously by Kwiatkowski, J., and Cheryan, M., Recovery of corn oil from ethanol extracts of ground corn using membrane technology, JAOCS 82, 221-227, 2005. Thus, the impurities may be either fine fiber (since it passed through the 11-µm pores of the Whatman filter paper #1) or sugar and/or soluble starch with a strong affinity for the polyamines.

All three feed streams in FIG. 2 showed similar elution patterns with the LH-20 resin: zein eluted first, followed by the "impurities", and finally the xanthophylls. All chromatograms showed a small xanthophylls peak in the void volume, implying some binding of zein and xanthophylls. The Showa zein had a negligible amount of xanthophylls and low molecular weight impurities (MW<4 kDa). The Freeman yellow zein showed a prominent xanthophylls peak and negligible impurities peak. The corn extract showed abundant xanthophylls, impurities, and zein.

Figure 3:
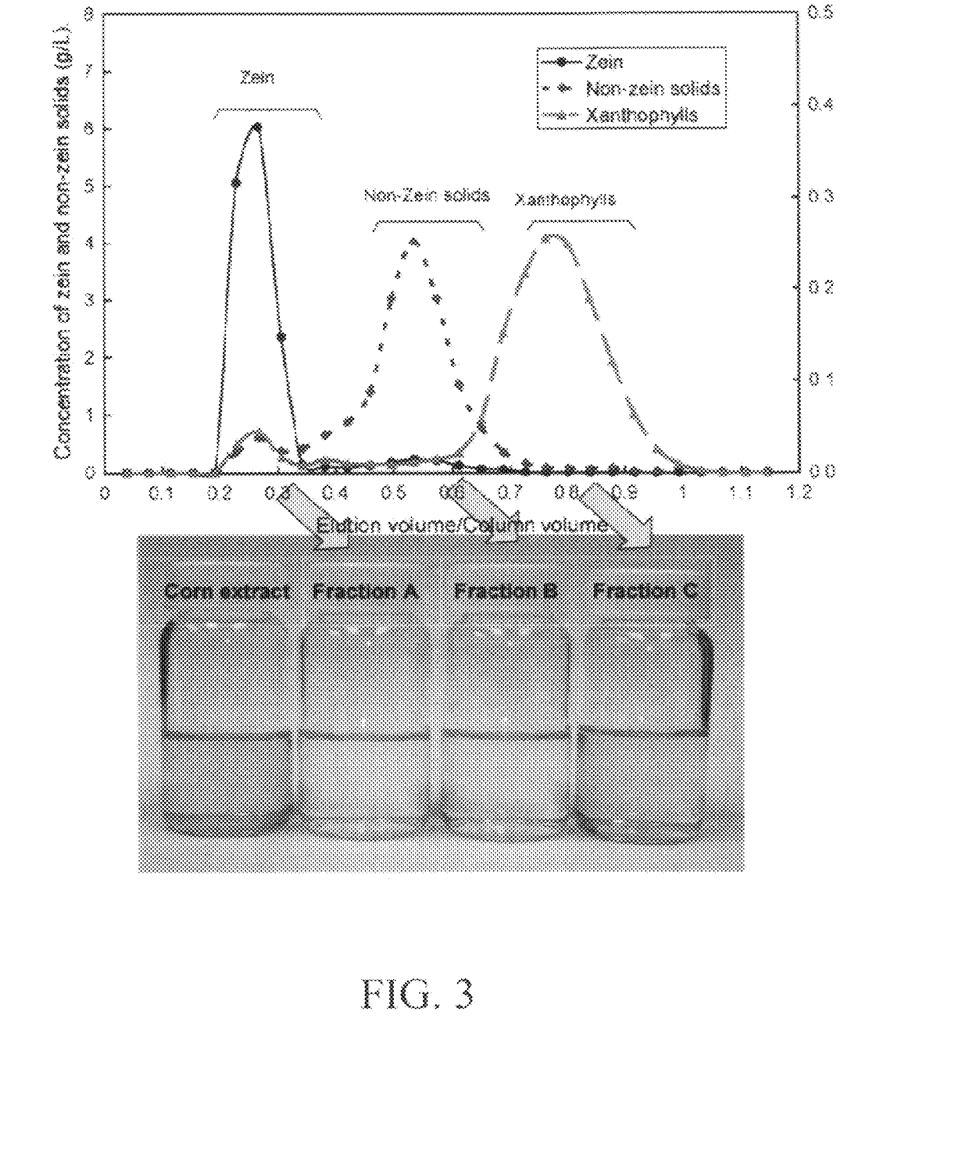
FIG. 3 is a chromatogram with associated fractions of corn extract at 25° C., using an eluent of 70% ethanol at 6.25 mL/min, feed injection of 50 mL corn extract, and fraction sizes of 3 min or 18.75 mL each.

The individual fractions from the corn extract were further analyzed for protein and total solids content. The results are shown in FIG. 3 together with photographs of the samples. This type of analysis reveals three peaks. The void volume fractions (termed Fraction A) are abundant in zein. The large peak of solids following the zein protein peak, which eluted before the xanthophylls, contained a significant amount of non-zein and non-xanthophylls solids. This "impurities" fraction is shown as Fraction B. Fractions beyond 50% column volume elution are rich in xanthophylls, and these are termed Fraction C. The corn extract, which was the feed to the column, is shown on the left of FIG. 3, and is a typical yellow color. The zein fraction was substantially de-colored and was white in color when dried, while the xanthophylls fraction (the sample on the right in FIG. 3) had a distinct yellow color characteristic of xanthophylls.

The operating conditions of this run resulted in baseline separation of the zein and impurities. The total solids and protein peaks almost completely overlapped in the zein fraction, indicating a high purity of zein. There was a small xanthophylls peak appearing in the zein fraction, which is due to strong hydrophobic interactions between zein and xanthophylls. This may be eliminated, for example, by modifying the mobile phase. There was also a small overlap of the impurities and xanthophylls. This can be eliminated by, for example, increasing the column length, but column length is limited by resin instability.

Table 1 summarizes the material balance of the experiment shown in FIG. 3.

TABLE 1

Yield and purity of zein and xanthophylls by chromatography (Omnifit column)

|  | Corn Extract | Zein Fraction | Impurities fraction | Xanthophylls fraction |
| --- | --- | --- | --- | --- |
| Volume (mL) | 50 | 80 | 180 | 200 |
| Total solids (g/L) | 14.2 | 4.4 | 1.9 | 0.095 |
| Zein purity (%) | 49 | 91 | 7.5 | 9.1 |
| Yield of zein (%) | 100 | 92 | 7.3 | 0.5 |
| Yield of xanthophylls (%) | 100 | 6.5 | 5.9 | 87 |

Zein and xanthophylls are extracted from 100 g of corn with 400 mL of 70% aqueous ethanol at 50° C. in 30 min. Filtering the corn slurry resulted in about 325 mL of the corn extract with a total solids (TS) of 14.2 g/L, of which 700 mg was zein (i.e., zein purity of the extract was ~49%). Fifty milliliters of this extract was injected into the column, and eluted with 460 mL of mobile phase (70% ethanol). Fraction A was 80 mL in volume and had TS of 4.4. g/L, of which 91% was zein, resulting in a yield of over 90% of the zein in the extract. The rest of the zein appeared in Fractions B and C. Fraction C was 200 mL in volume, contained about 0.1 g/L TS and 88% of the xanthophylls in the extract. It may be noted that the total solids material balance does not close, and this could be attributed to the accuracy of measuring the total solids in Fraction C. There is still evidence of zein-xanthophylls binding, since 6% of the xanthophylls appeared in Fraction A and 7.3 and 0.5% of the zein appeared in Fractions B and C, respectively. The substantial removal of the xanthophylls from the zein resulted in a white-colored zein, which is highly desirable for pharmaceutical and other selected applications. The impurities elute before the xanthophylls, resulting in pure (~90%) zein and xanthophylls fractions. Thus, starting with 17 g of corn or 50 mL corn extract, one can obtain 320 mg of zein with 90+% yield and purity using this exemplary method.

Figure 4:
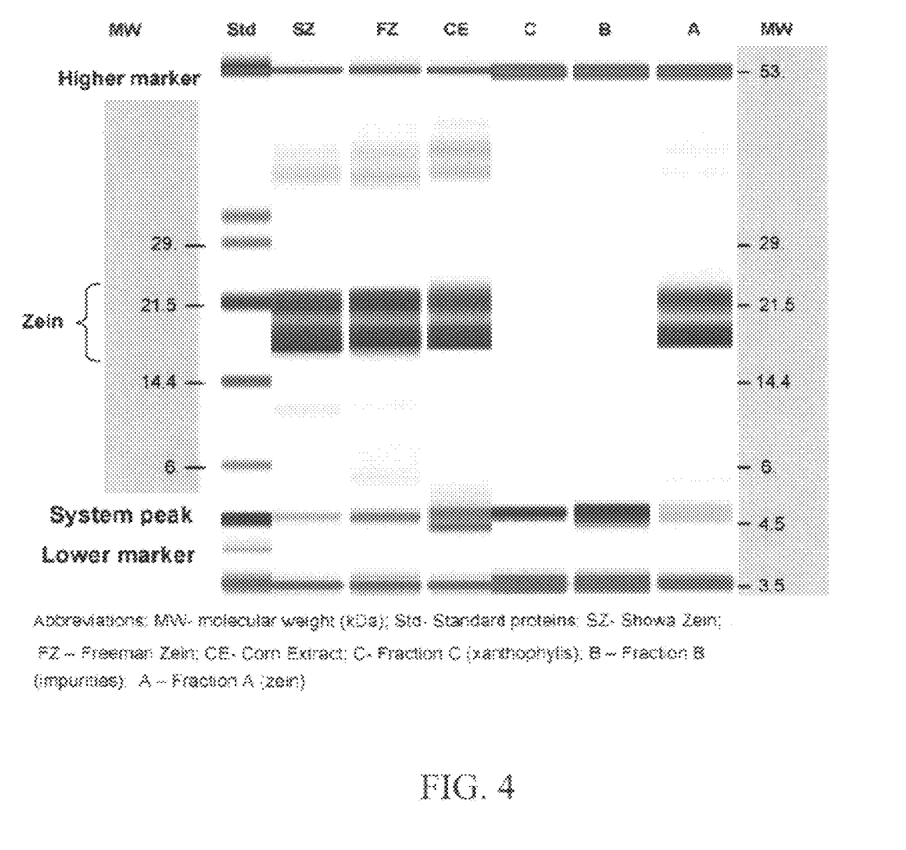
FIG. 4 is a gel electophoresis output for corn fractions (including xanthophylls, impurities, and zein) and commercial zeins, including Showa zein, Freeman zein, and corn extract.

To confirm these results, the fractions from the Omnifit column were subjected to electrophoresis using the Agilent 2100 Bioanalyzer with the Protein 50 kit. A comparison of the corn extract and the three fractions from the column along with the commercial zeins is shown in FIG. 4. The commercial zeins, the corn extract, and Fraction A show a set of bands at a molecular weight of 21,000-22,000, which represents alpha-zein. There is also a set of minor bands visible in the 44,000-48,000 region, which could be dimers of alpha-zein. Lower molecular weight zeins are barely visible, but this could be because of their low concentrations. The impurities and the xanthophylls fractions showed no zein bands. This implies that the reduction in zein yield as observed in Table 1 may be due to accounting of non-protein nitrogen, which are generally low molecular weight compounds that may be expected to elute in Fractions B and C.

Figure 5:
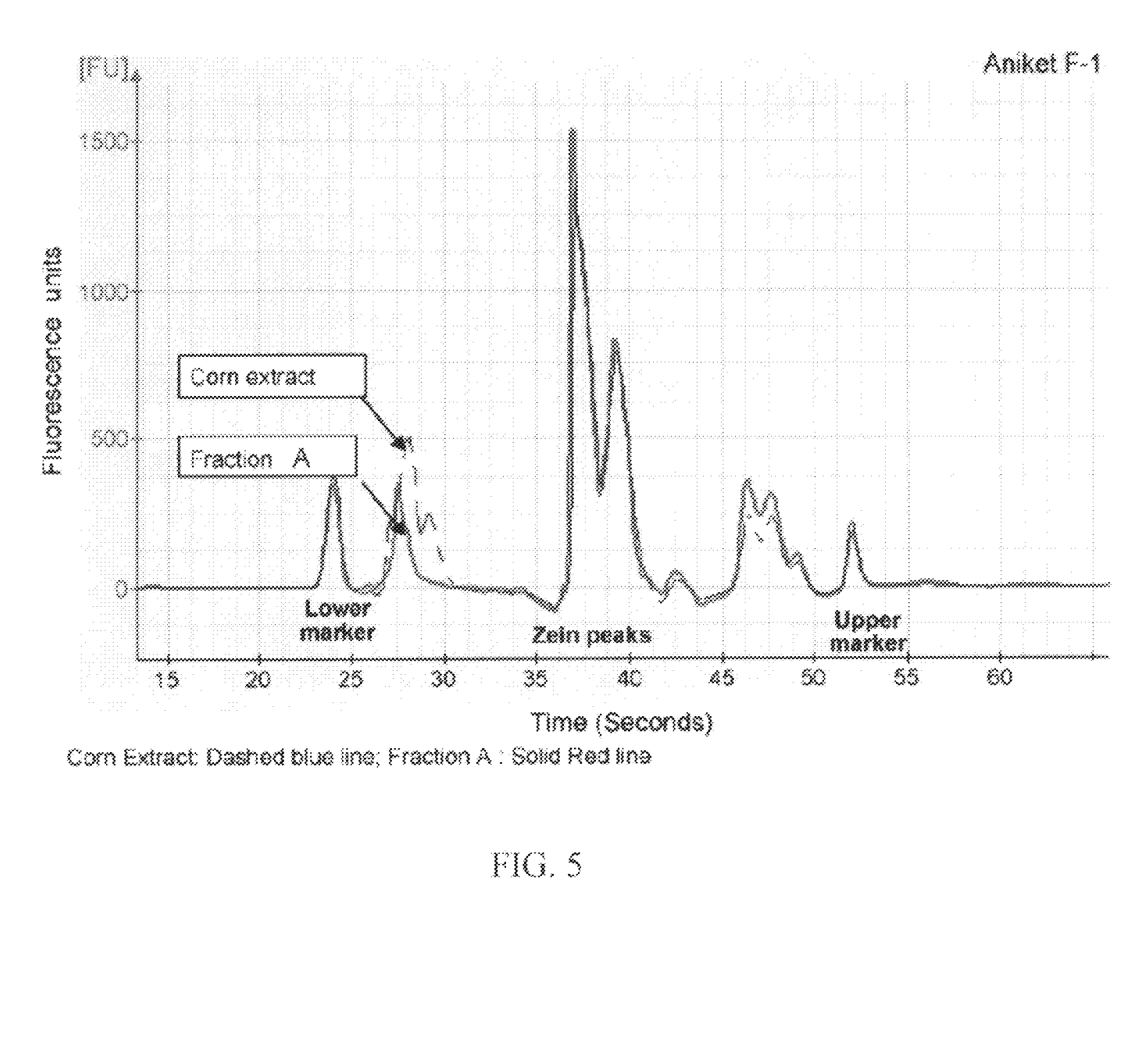
FIG. 5 is a set of overlapped elecropherograms of zein fraction (Fraction A of FIG. 4) and corn extract obtained from gel electrophoresis.

FIG. 5 shows the electropherograms of the Fraction A and the corn extract on the same plot. There is almost a perfect overlap of the two electropherograms confirming that Fraction A contains essentially all of the zeins in the extract. This confirms the zein purity and yield data in Table 1.

Figure 6:
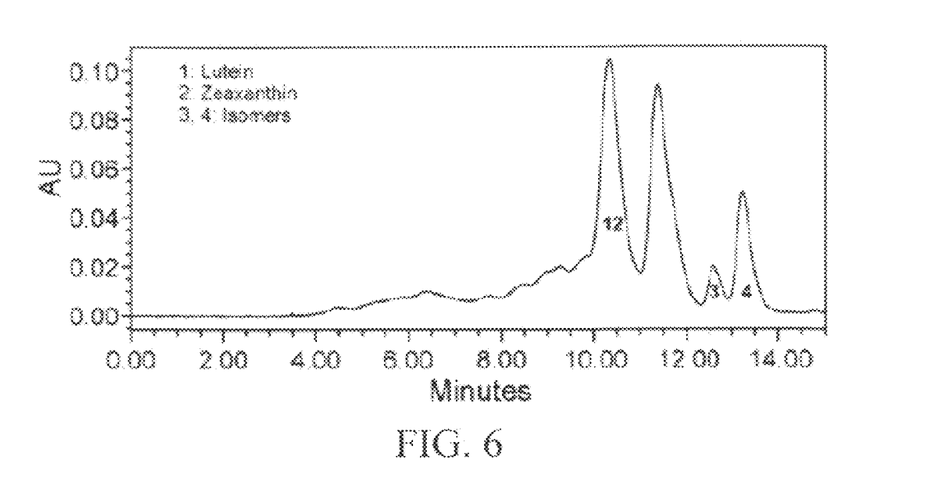
FIG. 6 shows HPLC analysis of membrane-concentrated xanthophylls (Fraction C) obtained as shown in FIG. 3, having a detection of 450 nm.

The purity of the xanthophylls in Fraction C was evaluated by HPLC as shown in FIG. 6. Fraction C showed four peaks. Peaks 1 and 2 match the spectra of standard lutein and zeaxanthin respectively. This was further confirmed from the peak spectra (FIG. 7), which also showed four peaks. The others may be beta-cryptoxanthin or isomers of xanthophylls. Since peak maxima of each compound also vary with the solvent, it is difficult to exactly identify the compounds eluting in Peaks 3 and 4. The spectra seems to indicate they are carotenoids.

Figure 8:
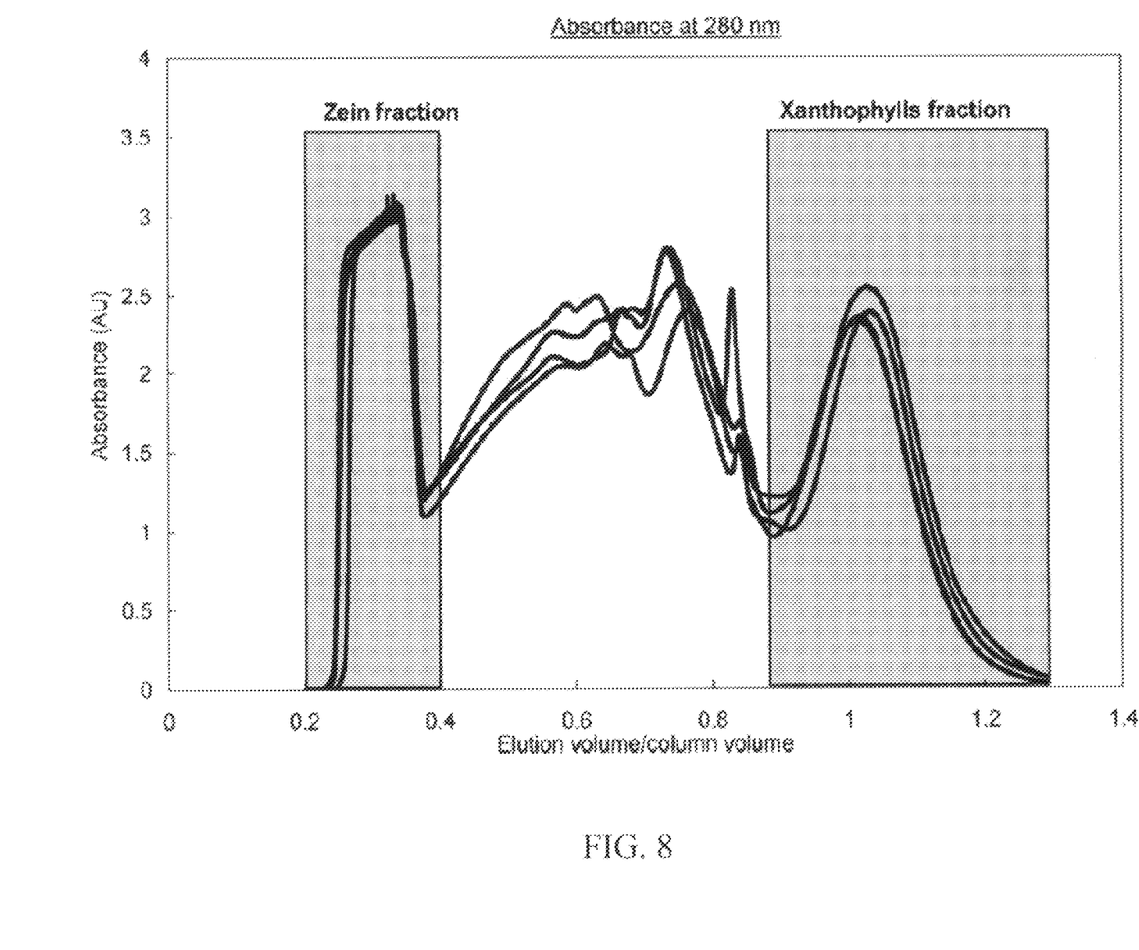
FIG. 8 shows reproducibility of an exemplary chromatography process according to embodiments of the present invention, including repeated injections of corn extract into an Omnfit column with LH-20 resin.

The reproducibility of the separation was tested using different batches of corn extracts. The chromatograms of five of those trials are shown in FIG. 8. The substantial overlap in the chromatograms are a good indication of the reliability of the exemplary method for producing substantially pure zein and xanthophylls.

EXAMPLE 2

The corn extract was preconcentrated by membrane concentration (MC) to improve the productivity of the chromatography step. Several nanofiltration and/or reverse osmosis membranes are available for this purpose, such as the DK from GE and SW30 from FilmTec. The concentration was performed in a dead end type Amicon cell at 50° C. and 400 psi to a concentration factor of 16×. The corn extract had an initial total solids of 15 g/L and an average flux of 5 liters per square meter per hour (LMH). Rejection of the solids was over 99%. The permeate was essentially colorless and can be recycled.

To investigate the effect of mass loading on column productivity, the 16× corn extract was diluted with various volumes of 70% ethanol and injected onto the Tricom column containing the LH-20 resin. The mobile phase for these experiments was 70% ethanol, as described earlier in Example 1. Ten mL fractions were collected after the void volume and analyzed for total solids and nitrogen content. With an 8× concentrated corn extract, the zein yield was 85%, and zein purity was 97%. Thus, the productivity of the chromatographic separation step could increase by at least eight times if the feed is preconcentrated, resulting in lower solvent consumption and resin costs.

EXAMPLE 3

To demonstrate the post-chromatography membrane concentration step, the fractions from the LH20 column shown in Table 1 were concentrated by membrane concentration (e.g., steps 113, 119, and 125 in FIG. 1). Several nanofiltration and/or reverse osmosis membranes are available for this purpose, such as the DK from GE and SW30 from FilmTec. The concentration was performed in a dead end type Amicon cell at 50° C. and 400 psi to a concentration factor of 15×. The zein fraction, with initial total solids of 4 g/L resulted in a flux of 10 liters per square meter per hour (LMH), while the xanthophylls fraction (0.1 g/L) had an average flux of 15 LMH with the SW30 membrane. Rejection of the solids in all cases was over 99%. The permeate in these concentration experiments was essentially colorless and can be recycled.

Figure 7:
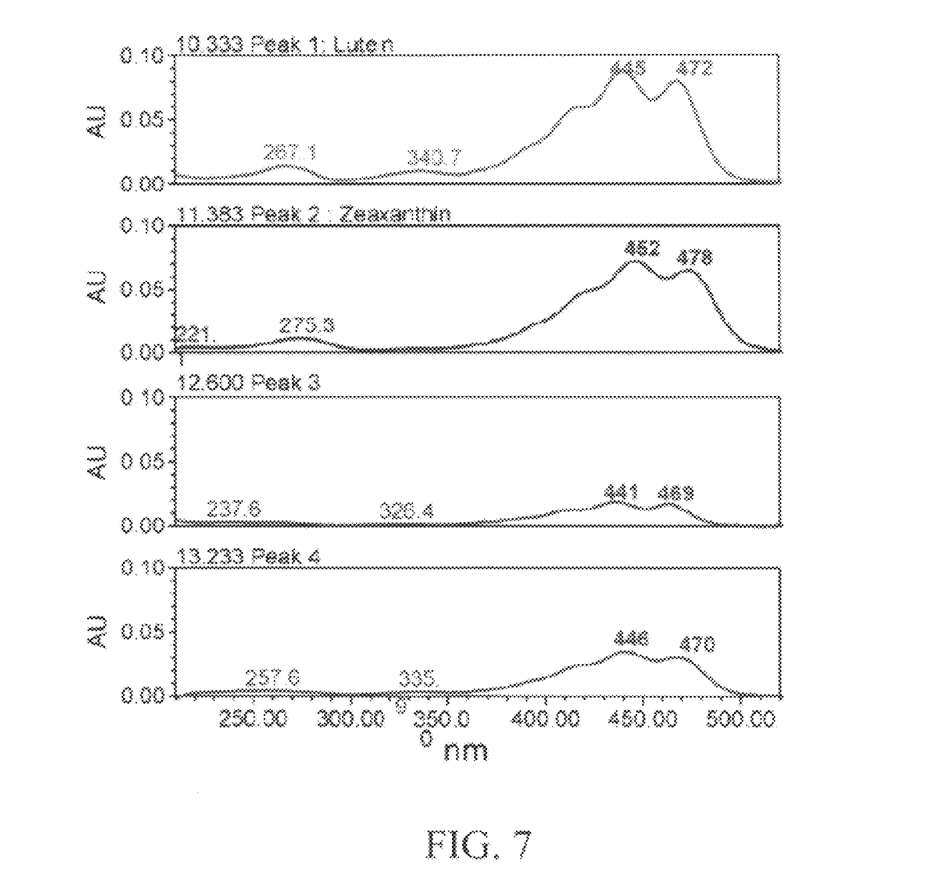
FIG. 7 is peak spectra of the four peaks obtained in the HPLC analysis of xanthophylls Fraction C shown in FIG. 6.

To further show that the xanthophylls fraction did indeed consist of the main corn-derived xanthophylls (lutein and zeaxanthin), the above membrane-concentrated xanthophylls fraction was analyzed by an improved HPLC method of E. E. Moros et al. This method was improved by eliminating the binary and ternary solvent mixtures and instead using single solvents with a simpler gradient pattern and eliminating sample preparation steps. As shown in FIG. 7, both lutein and zeaxanthin were identified in the "xanthophylls fraction" (peaks 1 and 2). Two other peaks were also visible, which could be additional isomers of lutein.

EXAMPLE 4

Another method of post-chromatography concentration is adsorption chromatography (AC in FIG. 1). Several commercially available adsorbents, such as activated carbons, diatomaceous earths, activated alumina, silica, zeolite, magnesia, Rohm and Hass XAD resins, Mitsubishi HP and SP resins, were tested, and their adsorption-desorption properties were determined for xanthophylls using standard batch methods known in the literature for determination of adsorption isotherms. One of the best resins was the HP20 resin from Mitsubishi, which gave an equilibrium concentration of 20 mg xanthophylls adsorbed per gram of the adsorbent. In our example with the single-strength extract, this implies that each gram of resin can adsorb xanthophylls from 16 liters of the xanthophylls fraction.

The resin was packed in a Tricom column of 1 cm inner diameter and 20 cm length. The eluent stream was continuously monitored at 450 nm. The column was loaded with 60 mL of the xanthophylls fraction, and ethyl acetate was used as the mobile phase at room temperature and a flow rate of 2 mL/min. The bound xanthophylls were eluted in one column volume (15 mL) of ethyl acetate. In another experiment, the column was loaded with 10 mL of a 4% xanthophylls solution and eluted with ethyl acetate at room temperature and a flow rate of 2 mL/min. The bound xanthophylls were eluted in two column volumes (30 mL) of ethyl acetate. Thus, adsorption chromatography may also be used as a post-chromatography step to concentrate the fractions.

Thus, preferred embodiments of the present invention provide an efficient, flexible, and simple process for production of highly pure zein from corn, and further provide a method for simultaneously producing substantially pure xanthophylls from the same extract of corn. Preferred methods have one or more of several advantages. For example, the purified products may by produced in one separation step. All processing, including extraction, elution, and concentration, may be done using the same solvent if desired. It is possible to perform steps of the present invention using only in-house raw materials available in a typical dry-grind ethanol plant. High zein yields of 90% or greater, and/or zein purity of 90% or greater may be obtained. Purified zein may be substantially decolorized and white in appearance.

It should be understood that, as used herein, the term "membrane technology" may refer to the appropriate membrane, whether it is microfiltration, ultrafiltration, nanofiltration, or reverse osmosis, and that diafiltration may be used when necessary to purify the solids or to enhance recovery of product, and that combinations of the above-mentioned processes may be necessary. Although use of column chromatography is described in the Examples above, batch chromatography using the resin in a mixed vessel may also be used.

Further, though nanofiltration is described, one skilled in the art can substitute what the art terms "reverse osmosis" or "tight ultrafiltration" or "ultrafiltration" membranes to achieve substantially the same or comparable results.

The various embodiments described in the present invention should not be construed as being restrictive, in that other modifications, substitutions and alternatives to specific equipment and methods are possible and known to those ordinarily skilled in the art. Such modifications, substitutions and alternatives can be made without departing from the spirit and scope of the invention, which should be determined from the appended claims.

Various features of the present invention are set forth in the appended claims.

The invention claimed is:

1. A process for producing zein and xanthophylls from corn, the process comprising:
    extracting soluble compounds from a corn-based material with wan alcohol solvent to provide a corn-solvent mixture, the soluble compounds comprising at least zein and xanthophylls;
    first separation of the corn-solvent mixture into two streams, of which one stream is an extract containing substantially the zein, impurities, xanthophylls and solvent, wherein the impurities comprise substantially all components in the extract other than solvent, zein and xanthophylls, and another stream containing the remaining corn solids and solvent, said first separation comprising at least one of centrifugation, filtration, and membrane microfiltration;
    second separation of a zein fraction and a xanthophylls fraction from the extract containing substantially the zein, impurities, xanthophylls and solvent to provide an eluted zein fraction and an eluted xanthophyll fraction, said second separation comprising chromatography based on a size-exclusion mechanism;
    concentrating the separated zein fraction eluted from said second separation by removing the solvent; and
    concentrating the separated xanthophylls fraction eluted from said second separation by removing the solvent.

2. The process of claim 1,
    wherein said second separation separates the separated zein fraction and the separated xanthophylls fraction in a single step.

3. The process of claim 2, wherein said concentrating the separate zein comprises nanofiltration.

4. The process of claim 2, wherein said concentrating the separate zein comprises using reverse osmosis.

5. The process of claim 2, wherein said concentrating the separated zein comprises using adsorption chromatography.

6. The process of claim 5, wherein a mobile phase used for elution in the adsorption chromatography comprises ethyl acetate.

7. The process of claim 1, further comprising:
    before said second separation, concentrating the extract to provide a higher level of solids in a concentrated extract, wherein said concentrating comprises membrane filtration;
    wherein said second separation separates said concentrated extract.

8. The process of claim 7, wherein said concentrating the extract further comprises dehydration.

9. The process of claim 1, further comprising:
    before said second separation, concentrating the extract to provide a higher level of solids in a concentrated extract, wherein said concentrating comprises membrane filtration, wherein said second separation separates said concentrated extract.

10. The process of claim 1, wherein the alcohol is aqueous ethanol.

11. The process of claim 10, wherein the alcohol is aqueous ethanol including a mixture of 60-100% ethanol by volume and water.

12. The process of claim 1, wherein said extraction comprises at least one of batch and continuous extraction.

13. The process of claim 1, wherein said first separation comprises centrifugation.

14. The process of claim 1, wherein said first separation comprises filtration.

15. The process of claim 1, wherein said first separation comprises membrane microfiltration.

16. The process of claim 1, wherein chromatographic media used in said second separation has a molecular weight exclusion limit of 10,000 or less.

17. The process of claim 16 wherein the chromatographic media has a molecular weight exclusion limit of 5000 or less.

18. The process of claim 1, wherein the solvent is aqueous ethanol, and wherein a mobile phase used in said second separation to elute the fractions comprises aqueous alcohol.

19. The process of claim 1, further comprising:
fractionating the impurities after said second separation.

20. The process of claim 1, wherein the corn-based material comprises at least one of corn gluten meal, distillers dried grains with or without solubles, and corn-based materials that have been partially or substantially de-oiled.

21. The process of claim 1, wherein the separated zein has a purity of at least 90%.

22. A process for producing zein and xanthophyll from corn, the process comprising:
extraction of soluble compounds from a corn-based material with an aqueous ethanol solvent to provide a corn-solvent mixture, the soluble compounds comprising at least zein and/or xanthophylls;
first separation of the corn-solvent mixture into two streams, of which one stream is an extract containing substantially the zein, xanthophylls, impurities, and solvent, and another stream containing the remaining corn solids and solvent, said first separation comprising at least one of centrifugation, filtration, and membrane microfiltration, wherein the impurities comprise substantially all components in the extract other than solvent, zein, and xanthophylls;
second separation of a zein fraction and a xanthophylls fraction from the extract comprising the impurities in a single step, said second separation comprising chromatography based on a size-exclusion mechanism, wherein said second separation uses a mobile phase comprising aqueous ethanol;
concentrating the separated zein fraction eluting from the column by removing the solvent;
concentrating the separated xanthophyll fraction eluting from the column by removing the solvent; and
recycling the aqueous ethanol from the mobile phase.

23. The process of claim 22, wherein the aqueous ethanol in both said extraction and said second separation have substantially the same ethanol concentration.

24. The process of claim 22, wherein the aqueous ethanol in both said extraction and said second separation have an ethanol concentration of about 70-95%.

25. The process of claim 22, further comprising:
recycling ethanol from at least one of said extraction, said first separation, said concentrating the separated zein fraction, and said concentrating the separated xanthophyll fraction.

26. The process of claim 1, wherein the corn comprises whole ground corn.

27. The process of claim 22, wherein the corn comprises whole ground corn.

28. The process of claim 1, wherein said second separation occurs directly from the extract resulting from said first separation.

* * * * *

UNITED STATES PATENT AND TRADEMARK OFFICE
CERTIFICATE OF CORRECTION

PATENT NO. : 8,236,929 B2
APPLICATION NO. : 11/990471
DATED : August 7, 2012
INVENTOR(S) : Munir Cheryan et al.

It is certified that error appears in the above-identified patent and that said Letters Patent is hereby corrected as shown below:

In the Claims:

Col. 14, line 21   After "with", please delete "wan" and insert -- an -- therefor.

Signed and Sealed this
First Day of October, 2013

Teresa Stanek Rea
*Deputy Director of the United States Patent and Trademark Office*